United States Patent [19]

Adolfsen et al.

[11] Patent Number: 5,631,167
[45] Date of Patent: May 20, 1997

[54] CAPSULE CHEMISTRY ANALYTICAL METHODS EMPLOYING DIOXETANE CHEMILUMINESCENCE

[75] Inventors: Robert F. Adolfsen, Montrose, N.Y.; Hashem Akhavan-Tafti, Sterling Heights, Mich.; Renuka De Silva, Northville, Mich.; A. Paul Schaap, Grosse Pointe Park, Mich.

[73] Assignees: Bayer Corporation, Tarrytown, N.Y.; Board of Governors Wayne State Univ., Detroit, Mich.

[21] Appl. No.: 509,692

[22] Filed: Jul. 31, 1995

[51] Int. Cl.⁶ .......................... G01N 35/08; G01N 21/76
[52] U.S. Cl. .................. 436/53; 436/63; 436/166; 436/172; 436/501
[58] Field of Search .................. 436/53, 166, 63, 436/172, 501

[56] References Cited

U.S. PATENT DOCUMENTS

| | | | |
|---|---|---|---|
| 4,742,010 | 5/1988 | Lin et al. | 436/164 X |
| 4,952,707 | 8/1990 | Edwards | 549/221 |
| 4,959,182 | 9/1990 | Schaap | 252/700 |
| 4,962,192 | 10/1990 | Schaap | 536/18.1 |
| 5,004,565 | 4/1991 | Schaap | 252/700 |
| 5,013,827 | 5/1991 | Schaap | 536/17.3 |
| 5,032,381 | 7/1991 | Bronstein et al. | 424/9 |
| 5,068,339 | 11/1991 | Schaap et al. | 548/110 |
| 5,112,960 | 5/1992 | Bronstein | 536/18.1 |
| 5,145,772 | 9/1992 | Voyta | 435/4 |
| 5,220,005 | 6/1993 | Bronstein | 536/26.21 |
| 5,225,584 | 7/1993 | Brooks et al. | 558/189 |
| 5,248,618 | 9/1993 | Haces | 436/172 |
| 5,268,147 | 12/1993 | Zabetakis et al. | 422/82 |
| 5,393,469 | 2/1995 | Akhavan-Tafti | 252/700 |
| 5,399,497 | 3/1995 | Kumar et al. | 436/53 |
| 5,451,347 | 9/1995 | Akhavan-Tafti et al. | 252/700 |

FOREIGN PATENT DOCUMENTS

| | | |
|---|---|---|
| 473984 | 3/1992 | European Pat. Off. . |
| 0473984 | 3/1992 | European Pat. Off. . |
| 0630884 | 12/1994 | European Pat. Off. . |
| 8800695 | 1/1988 | WIPO . |
| 9410258 | 5/1994 | WIPO . |
| 9421821 | 9/1994 | WIPO . |
| 9426726 | 11/1994 | WIPO . |

OTHER PUBLICATIONS

W. Adam et al. *Chem. Bev.* 1987, 120, 1565–1571.

S. Beck et al. *Anal. Chem.* 1990, 62, 2258–2270.

Schaap, A.P., et al., *Tetrahedron Lett.*, 28(9), 935–8 (1987).

Schaap, A.P., et al., *Tetrahedron Lett.*, 28(11), 1159–62 (1987).

Schaap, A.P., *Photochem. Photobiol.*, 47S, 50S (1988).

Schaap, A.P., *Clinical Chemistry*, 35(9), 1863–4 (1989).

Martin Josso, Ph.D. Thesis, Wayne State Univ. (1992), Diss. Abs. Int., vol. 53, No. 12B, p. 6305.

*Primary Examiner*—Arlen Soderquist
*Attorney, Agent, or Firm*—Richard S. Handley

[57] ABSTRACT

Improved assay methods utilizing stable, enzymatically triggered chemiluminescent 1,2-dioxetanes with improved water solubility are provided. Assays are performed by a capsule chemistry analytical assay method wherein fluid capsules comprising discrete aqueous segments containing either a chemiluminescent dioxetane reagent or an activating agent separated by an oil-based isolating fluid are flowed through a conduit, and subsequently reacted to produce light.

The improvement comprises using a dioxetane substituted with two or more water-solubilizing groups disposed on the dioxetane structure to provide the chemiluminescence. Compositions comprising such a dioxetane, a non-polymeric surfactant enhancer and optionally a fluorescer, provide enhanced chemiluminescence and eliminate the problem of reagent carryover when used in assays performed on capsule chemistry analytical systems.

17 Claims, 4 Drawing Sheets

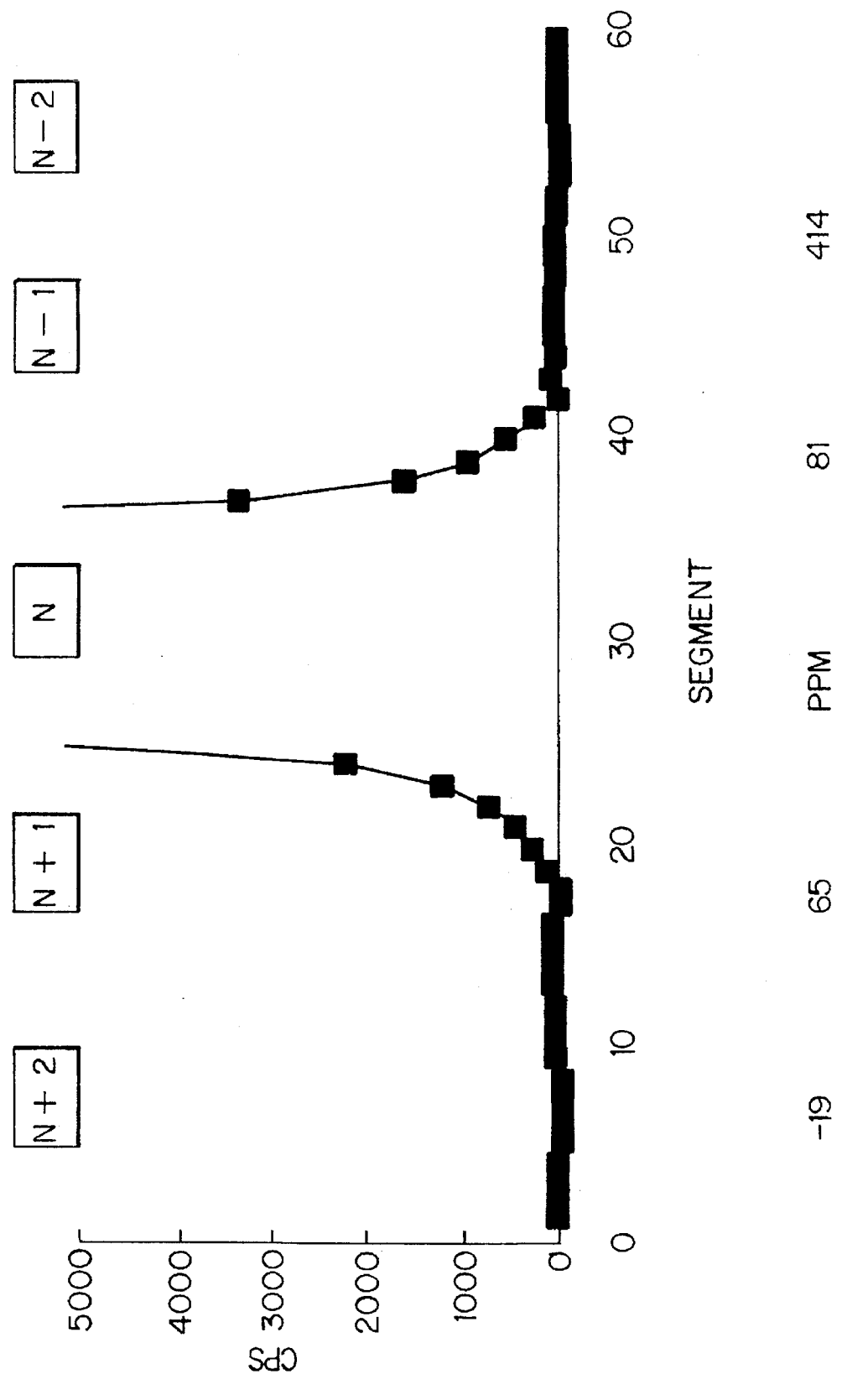

CAPSULE CHEMISTRY ANALYTICAL METHODS EMPLOYING DIOXETANE CHEMILUMINESCENCE

BACKGROUND OF THE INVENTION

(1) Field of the Invention

The present invention relates to stable 1,2-dioxetanes and compositions which can be triggered by chemical reagents, including enzymes, to generate chemiluminescence. The dioxetanes contain more than one ionizable group which are part of an alkoxy substituent. Compositions used in the practice of the invention contain a stable dioxetane as described above, a cationic surfactant and optionally a fluorescer which enhance the amount of chemiluminescence which is produced. Dioxetanes and enhanced compositions of the present invention are useful in methods for generating light (chemiluminescence) and in methods of analysis for detecting the presence or amount of an analyte. Importantly, the ionizable groups afford a more water soluble dioxetane and solve an unexpected chemical carryover problem in capsule chemistry analytical systems.

(2) Description of Related Art a. Enzymatically Triggerable Dioxetanes

The first examples of enzymatic triggering of dioxetanes are described in a U.S. patent application (A. P. Schaap, U.S. patent application Ser. No. 887,139) and a series of papers (A. P. Schaap, R. S. Handley, and B. P. Giri, Tetrahedron Lett., 935 (1987); A. P. Schaap, M. D. Sandison, and R. S. Handley, Tetrahedron Lett., 1159 (1987) and A. P. Schaap, Photochem. Photobiol., 47S, 50S (1988)). The highly stable adamantyl-substituted dioxetanes bearing a protected aryloxide substituent are triggered to decompose with emission of light by the action of both an enzyme and aqueous buffer to give a strongly electron-donating aryloxide anion which dramatically increases the rate of decomposition of the dioxetane. As a result, chemiluminescence is emitted at intensities several orders of magnitude above that resulting from slow thermal decomposition of the protected form of the dioxetane. U.S. Pat. No. 5,068,339 to Schaap discloses enzymatically triggerable dioxetanes with covalently linked fluorescer groups decomposition of which results in enhanced chemiluminescence via energy transfer to the fluorescer. U.S. Pat. Nos. 5,112,960 and 5,220,005 and a PCT application (WO88/00695) to Bronstein disclose triggerable dioxetanes bearing substituted adamantyl groups. U.S. Pat. No. 4,952,707 to Edwards discloses phosphate-substituted dioxetanes. A PCT application (WO94/26726) to Bronstein discloses adamantyl dioxetanes bearing a phenyl or naphthyl group substituted at a non-conjugated position with an enzyme labile OX group and with an additional group on the aryl ring.

Other triggerable dioxetanes are disclosed in a PCT application (WO94/10258) to Wang. The dioxetanes disclosed in Wang contain an alkoxy group which may be mono-substituted and a substituted phenyl-OX group wherein one or more non-hydrogen groups are present on the benzene ring substituent in addition to the triggerable OX group.

Dioxetanes disclosed in all of the foregoing publications generate a light-emitting carbonyl compound comprising an alkyl ester of an aromatic carboxylic acid, typically the methyl ester of a hydroxybenzoic or hydroxynaphthoic acid or else a hydroxyaryl ketone.

b. Surfactant Enhancement of Chemiluminescence from Triggerable Dioxetanes

Enhancement of chemiluminescence from the enzyme-triggered decomposition of a stable 1,2-dioxetane in the presence of water-soluble substances including an ammonium surfactant and a fluorescer has been reported (A. P. Schaap, H. Akhavan and L. J. Romano, Clin. Chem., 35(9), 1863 (1989)). Fluorescent micelles consisting of cetyltrimethylammonium bromide (CTAB) and 5-(N-tetradecanoyl) amino-fluorescein capture the intermediate hydroxy-substituted dioxetane and lead to a 400-fold increase in the chemiluminescence quantum yield by virtue of an efficient transfer of energy from the anionic form of the excited state ester to the fluorescein compound within the hydrophobic environment of the micelle.

U.S. Pat. Nos. 4,959,182 and 5,004,565 to Schaap describe additional examples of enhancement of chemiluminescence from chemical and enzymatic triggering of stable dioxetanes in the presence of micelles formed by the quaternary ammonium surfactant CTAB. Fluorescent micelles also enhance light emission from the base-triggered decomposition of hydroxy- and acetoxy-substituted dioxetanes.

U.S. Pat. No. 5,145,772 to Voyta discloses enhancement of enzymatically generated chemiluminescence from 1,2-dioxetanes in the presence of polymers with pendant quaternary ammonium groups alone or admixed with fluorescein. Other substances reported to enhance chemiluminescence include globular proteins such as bovine albumin and quaternary ammonium surfactants. Other cationic polymer compounds were marginally effective as chemiluminescence enhancers; nonionic polymeric compounds were generally ineffective and an anionic polymer significantly decreased light emission. A PCT application (WO 94/21821) to Bronstein describes the use of mixtures of the aforementioned polymeric quaternary ammonium surfactant enhancers with enhancement additives.

The enhancement and catalysis of a non-triggerable dioxetane by pyranine in the presence of CTAB is described (Martin Josso, Ph.D. Thesis, Wayne State University (1992), Diss. Abs. Int., Vol. 53, No. 12B, p. 6305).

U.S. Pat. No. 5,393,469 to Akhavan-Tafti discloses enhancement of enzymatically generated chemiluminescence from 1,2-dioxetanes in the presence of polymeric quaternary phosphonium salts optionally substituted with fluorescent energy acceptors.

European Patent Application Serial No. 94108100.2 discloses enhancement of enzymatically generated chemiluminescence from 1,2-dioxetanes in the presence of dicationic phosphonium salts. No documents disclose the combination of an anionic fluorescer and a dicationic enhancer for enhancing chemiluminescence from a triggerable dioxetane. No example of enhancement of substituted dioxetanes of the type of the present invention has been reported.

c. Triggerable Dioxetanes with Improved Water Solubility

The enzymatically triggerable dioxetanes are now undergoing widespread use as substrates for marker enzymes in numerous applications including immunoassays, gene expression studies, Western blotting, Southern blotting, DNA sequencing and the identification of nucleic acid segments in infectious agents. Despite the growing use of these compounds, there are limitations to there use in some assay methods. Triggerable dioxetanes which are more water-soluble are desirable. As shown in the structures below, it is especially desirable that the hydroxy dioxetane formed by the dephosphorylation of a phosphate dioxetane by alkaline phosphatase remain highly soluble in water and buffered solutions and in compositions containing chemiluminescence enhancing substances. Such dioxetanes and compositions are of importance in certain solution assay methods for detecting hydrolytic enzymes or conjugates of hydrolytic enzymes.

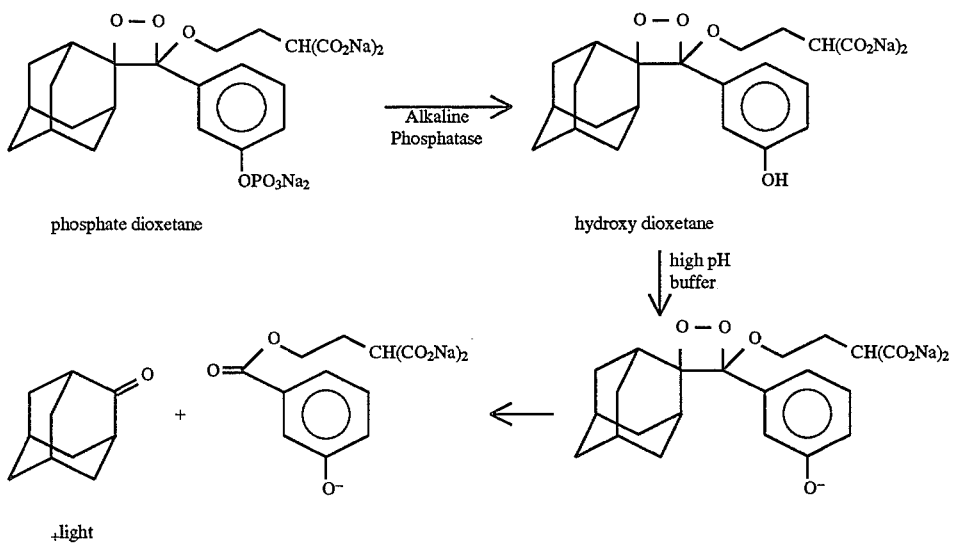

phosphate dioxetane hydroxy dioxetane

+light

As further background of the present invention and as more fully explained in the examples below, it has been found that use of conventional chemiluminescent dioxetane reagents in assays performed on automated instrumentation based on the principles of capsule chemistry analysis results in carryover of reagent from one fluid segment to another, resulting in potentially inaccurate measurements, erroneous results, and imprecision due to non-reproducibility. Capsule chemistry analysis is described in U.S. Pat. No. 5,399,497, which is fully incorporated by reference herein. It has been postulated that, among other possible means for overcoming the carryover problem, improved water solubility of the hydroxy dioxetane, in particular, might eliminate or minimize carryover of this luminescent reaction intermediate into adjacent fluid segments of a capsule chemistry analysis system.

Dioxetane compounds in commercial use do not incorporate any solubilizing groups which are appended to an alkoxy group. As such, these dioxetanes are unsuitable for use in assay methods requiring zero carryover. A suggestion of incorporating a solubilizing group into a dioxetane has been made (U.S. Pat. No. 5,220,005). A dioxetane with a carboxyl group substituted on an adamantyl substituent is claimed, however, the preparation of such a dioxetane is not described. Significantly, there is no disclosure of what effect the addition of a carboxyl group had, if any, on solubility and other properties of the dioxetane. There is no teaching in the art of how many solubilizing groups are required or what particular advantage might be conferred. Use of solubilizing groups which interfere with the removal of the protecting group which initiates light emission or which otherwise interfere with light production would be of no value. Solubilizing groups which would be removed during the luminescent reaction likewise would not be useful.

The present invention demonstrates surprisingly, that incorporation of one solubilizing group is insufficient to eliminate the carryover problem associated with the hydroxy dioxetane produced by dephosphorylation of a phosphate dioxetane. Phosphate dioxetanes whose hydroxy dioxetane product remains highly water soluble are provided herein to solve this problem. Further, enhanced compositions containing such phosphate dioxetanes are provided which produce efficient chemiluminescence when reacted with a triggering agent in an assay.

OBJECTS

It is an object of the present invention to provide stable, enzymatically triggered 1,2-dioxetanes with improved solubility in aqueous solution to produce chemiluminescence by the action of an enzyme. It is a second object of the present invention to provide 1,2-dioxetanes further substituted with two or more water-solubilizing groups disposed on the dioxetane structure. It is a further object of the present invention to provide a composition comprising a dioxetane with two or more water-solubilizing groups, a non-polymeric cationic enhancer and optionally a fluorescer, for providing enhanced chemiluminescence. It is a further object of the present invention to provide dioxetanes and compositions which, when used in assays performed on capsule chemistry analytical systems, eliminate the problem of reagent carryover.

IN THE DRAWINGS

FIG. 4 is a further profile of adjacent segments observed in the experiments which are more fully described in the Examples below and which established that the carryover was in fact chemical in nature.

DESCRIPTION OF THE PREFERRED EMBODIMENTS

Figure 1:
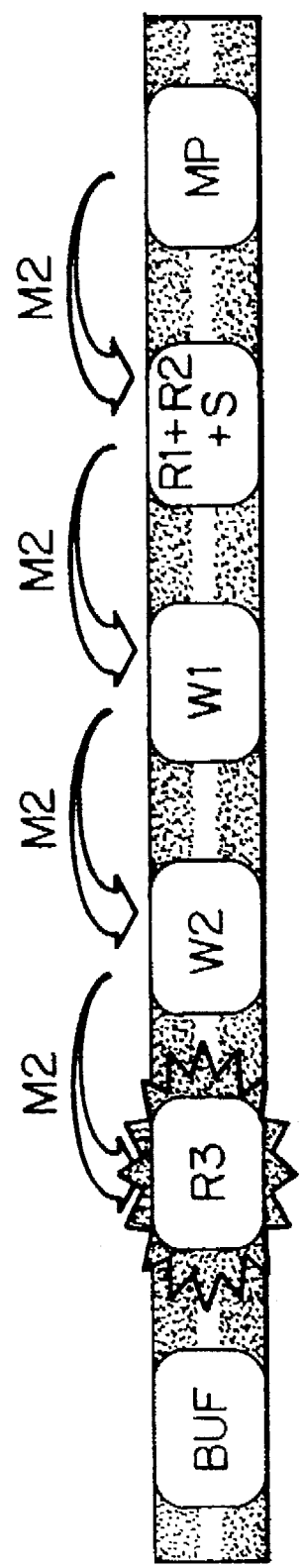
FIG. 1 is a diagram of a capsule chemistry analysis system in which carryover was determined to be a problem.

The present invention relates to triggerable dioxetanes with improved water solubility. Such triggerable dioxetanes eliminate or minimize carryover of the luminescent hydroxy dioxetane into adjacent segments in capsule chemistry analytical systems. Carryover can result from solubilization, deposition or precipitation of light-emitting material of low water solubility into the fluorocarbon oil which serves as the isolating fluid in capsule chemistry systems. Reagent carry-over can lead to inaccurate measurements, erroneous results and imprecision due to non-reproducibility.

The present invention relates to stable 1,2-dioxetanes which can be triggered by chemical reagents, including enzymes, to generate chemiluminescence. Stable dioxetanes useful in practicing the present invention may be of the formula:

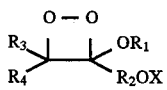

wherein $R_1$ is a hydrophilic organic group comprising a substituted alkyl, heteroalkyl, alkenyl or alkynyl group containing 1 to 20 carbon atoms, at least two groups which provide increased solubility in aqueous solution and optionally containing one or more atoms selected from the group consisting of oxygen, nitrogen, sulfur, phosphorus, halogen and alkali metals, wherein $R_3$ and $R_4$ are each selected from acyclic, cyclic and polycyclic organic groups which can optionally be substituted with heteroatoms and which provide stability to the dioxetane, wherein $R_2$ is an aryl ring group selected from phenyl and naphthyl groups which can include additional substituents and wherein X is a protecting group which can be removed by an activating agent to form an unstable oxide intermediate dioxetane compound which decomposes and releases electronic energy to form light and two carbonyl-containing compounds, one of which is an oxyanion-substituted ester compound containing the solubility increasing groups, according to the reaction:

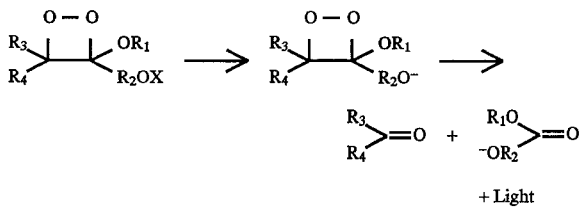

In one embodiment, the group $R_1$ is a straight or branched chain $C_1$ to $C_{20}$ alkyl group substituted with at least two groups which provide increased solubility in aqueous solution. Preferred solubilizing groups comprise groups which are substantially ionized under the conditions of use and include without limitation carboxylate, sulfonate, sulfate, phosphate, phosphonate, nitrate, trialkylammonium, trialkylphosphonium, dialkylsulfonium and guanidinium groups. Carboxylate groups are most preferred.

In a preferred embodiment, the group $R_1$ is a straight or branched chain $C_1$ to $C_8$ alkyl group substituted with at least two carboxylic acid or carboxylate salt groups including, for example, groups of the structure

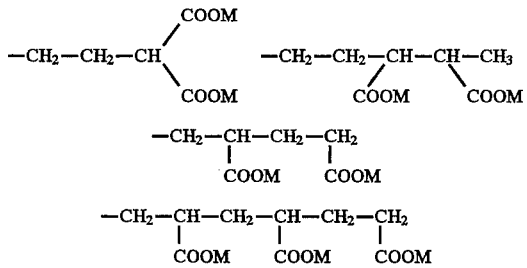

wherein M is selected from hydrogen, an alkali metal ion or a quaternary ammonium or phosphonium ion. When M is H it is recognized that the respective dioxetane compound will preferably only be used under conditions of pH where the carboxylic acid functions are ionized, i.e. $pH \geq$ about 7. Preferably M is a sodium or potassium ion.

In another embodiment, the group $R_1$ is a straight or branched chain heteroalkyl group substituted with at least two carboxylic acid or carboxylate salt groups including, for example, groups of the structure

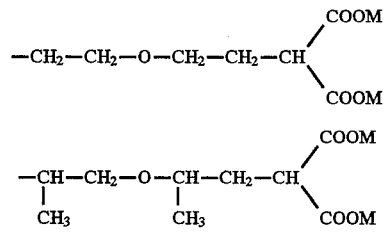

wherein M is as defined above.

The groups $R_3$ and $R_4$ in another embodiment are combined together in a cyclic or polycyclic alkyl group $R_5$ which is spiro-fused to the dioxetane ring, containing 6 to 30 carbon atoms which provides thermal stability and which can include additional non-hydrogen substituents.

The group $R_5$ is more preferably a polycyclic group, preferably an adamantyl group or a substituted adamantyl group having one or more substituent groups $R_6$ selected from halogens, alkyl, substituted alkyl, alkoxy, substituted alkoxy, carbonyl, carboxyl, phenyl, substituted phenyl, amino and alkylamino groups covalently bonded thereto.

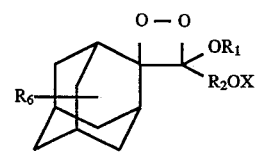

In another preferred embodiment the group $R_2$ is a phenyl or naphthyl group. It is especially preferred that $R_2$ is a phenyl group in which the OX group is oriented meta to the dioxetane ring group as shown below. The phenyl ring may contain additional ring substituents $R_7$ independently selected from halogens, alkyl, substituted alkyl, alkoxy, substituted alkoxy, carbonyl, carboxyl, amino and alkylamino groups. Some exemplary structures include by way of illustration

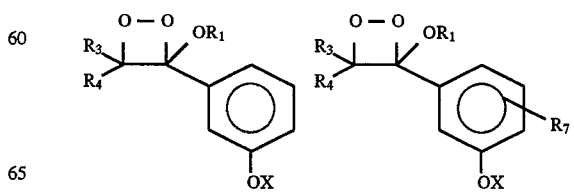

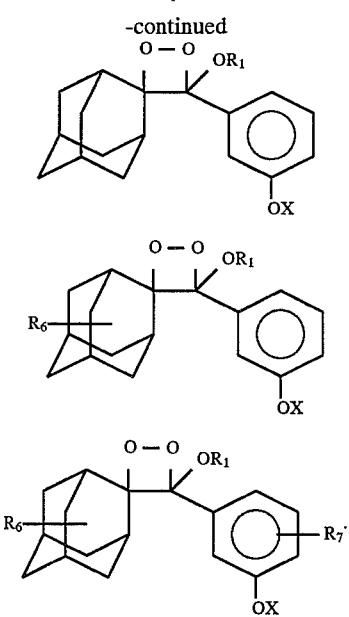

The OX group may be selected from hydroxyl, O⁻M⁺ wherein M is selected from hydrogen, an alkali metal ion or a quaternary ammonium or phosphonium ion, OOCR$_8$ wherein R$_8$ is selected from the group consisting of an alkyl and aryl groups containing 2 to 8 carbon atoms and optionally containing heteroatoms, $OPO_3^{-2}$ salt, $OSO_3^-$ salt, β-D-galactosidoxy and β-D-glucuronidyloxy groups. When the OX group is an ionic group such as $OPO_3^{-2}$ salt or $OSO_3^-$ salt, the water solubility increasing groups in R$_1$ must not also be this group. A particularly effective dioxetane compound for the chemiluminescent detection of alkaline phosphatase in aqueous solution is dioxetane 1 below. Hydroxy dioxetane 2 results from dephosphorylation of dioxetane 1.

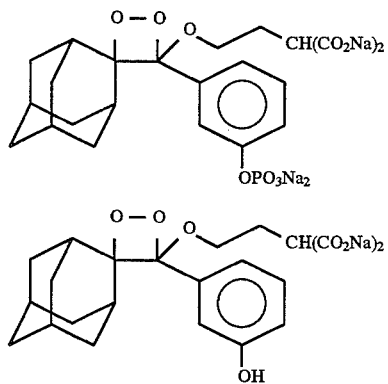

For comparison, dioxetane 3 which incorporates only one ionizable group was prepared. This dioxetane did not eliminate the carryover problem discussed above.

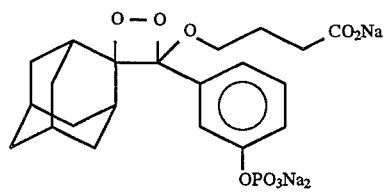

In another aspect of the invention, compositions providing enhanced chemiluminescence are provided. Enhanced compositions are advantageous in assays requiring the highest analytical sensitivity. Increasing the chemiluminescence efficiency of the dioxetane decomposition reaction while maintaining or reducing extraneous light emission from spontaneous dioxetane decomposition is one manner in which sensitivity can be enhanced or improved.

The present invention, therefore, also relates to compositions comprising a stable 1,2-dioxetane which can be triggered to generate chemiluminescence and an enhancer. Compositions for providing enhanced chemiluminescence comprise a dioxetane as described above in an aqueous solution, and a non-polymeric cationic enhancer substance which increases the quantity of light produced by reacting the dioxetane with the activating agent compared to the amount which is produced in the absence of the enhancer. It is preferred that the enhancer substance is a dicationic surfactant of the formula:

wherein each of A is independently selected from P and N atoms and wherein Link is an organic linking group containing at least two carbon atoms selected from the group consisting of substituted and unsubstituted aryl, alkyl, alkenyl and alkynyl groups and wherein Link may contain heteroatoms and wherein R is selected from lower alkyl or aralkyl containing 1 to 20 carbon atoms and wherein Y is an anion. It is especially preferred that the enhancer substance is a dicationic surfactant having the formula:

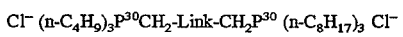

and wherein link is phenylene.

Compositions of the present invention for providing enhanced chemiluminescence may optionally contain at least one fluorescer as a supplementary enhancer. Fluorescers useful are those compounds which are capable of increasing the quantity of light produced through energy transfer. Anionic fluorescers are particularly effective it is believed due to favorable electrostatic interactions with the cationic enhancer. Particularly preferred fluorescers include, without limitation, pyranine and fluorescein.

EXAMPLES

Example 1

Preparation of Dioxetane 1

This dioxetane was prepared by the sequence of reactions described below. The synthesis up to the intermediate alkene [(3-hydroxyphenyl)-(2-iodoethoxy)methylene]tricyclo-[3.3.1.1³,⁷]decane was conducted essentially as described in U.S. Pat. Nos. 5,013,827 and 5,068,339.

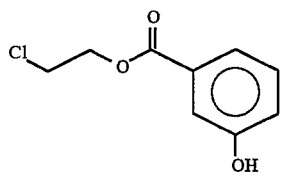

(a) Synthesis of 2-chloroethyl 3-hydroxybenzoate. A solution of 65 g of 3-hydroxybenzoic acid (0.47 mol) in 500 mL of 2-chloroethanol and 3 mL of H$_2$SO$_4$ was refluxed for 4 hours. The cooled solution was diluted with 500 mL of water and extracted with ethyl acetate (3×250 mL). The ethyl acetate was extracted twice with aqueous NaHCO$_3$ and then with water. The ethyl acetate solution was dried and evaporated under reduced pressure yielding 85 g of product as a thick oil; $^1$H NMR (CDCl$_3$) δ3.814 (t,2H, J=6 Hz), 4.569 (t,2H, J=6 Hz), 5.36 (br s,1H), 7.06–7.67 (m,4H).

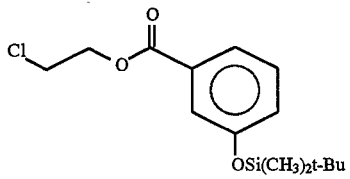

(b) Synthesis of 2-chloroethyl 3-t-butyldimethylsilyloxybenzoate. A solution of 10 g (50 mmol) the ester from step (a), t-butyldimethylsilyl chloride (8.25 g, 55 mmol) and imidazole (4.76 g, 70 mmol) in 100 mL of DMF was stirred under argon for 1 h. The solution was poured into 100 mL of water and extracted with ether (3×50 mL). The combined ether solutions were extracted with 20 mL of water. The organic layer was dried and evaporated giving 18 g of an oil which was purified by column chromatography using 0–2% ethyl acetate in hexane yielding 14.4 g of the product as a colorless oil (91%); $^1$H NMR (CDCl$_3$) δ0.218 (s,6H), 0.995 (s,9H), 3.81 (t,2H), 4.56 (t,2H), 7.05–7.65 (m,4H).

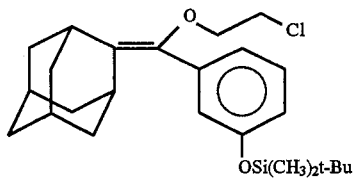

(c) Synthesis of [(2-chloroethoxy)-(3-t-butyldimethylsilyloxyphenyl)methylene]tricyclo[3.3.1.1$^{3,7}$]decane. A three neck flask was purged with argon and charged with 400 mL of anhydrous THF. Titanium trichloride (48 g, 0.3 mol) was added with stirring and the flask was cooled in an ice bath. Lithium aluminum hydride (6.0 g, 0.16 mol) was added in small portions causing a brief exothermic reaction. After all of the LAH was added, the cooling bath was removed and the mixture warmed to room temperature. Triethylamine (30 mL) was added and the black mixture was refluxed for 1.5 hours under argon. A solution of adamantanone (14 g, 93 mmol) and 2-chloroethyl 3-t-butyldimethylsilyloxybenzoate (10 g, 31 mmol) in 50 mL of dry THF was added dropwise while reflux was continued. After an additional 10 min, TLC (5% ethyl acetate in hexane) indicated conversion of the ester to new material so the mixture was cooled and diluted with 3 L of hexane. The hexane was decanted, filtered through filter paper and evaporated leaving an oil which was purified by column chromatography on silica gel, eluting with 0–3% ethyl acetate in hexane yielding 8.68 g of alkene (65% based on ester); $^1$H NMR (CDCl$_3$) δ0.195 (s,6H), 0.983 (s,9H), 1.78–1.98 (m,12H), 2.65 (br s,1H), 3.334 (br s,1H), 3.55 (t,2H), 3.66 (t,2H), 6.85–7.29 (m,4H).

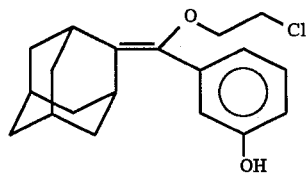

(d) Synthesis of [(2-chloroethoxy)-(3-hydroxyphenyl)methylene]tricyclo[3.3.1.1$^{3,7}$]decane. The silyl-protected alkene (8.0 g, 19 mmol) was dissolved in 100 mL of dry THF and reacted with 5.2 g of tetrabutylammonium fluoride. After stirring 15 min, the solution was evaporated and the residue partitioned between 100 mL of ether and 100 mL of water. The water solution was extracted with three 100 mL portions of ether. The combined organic solutions were washed with three 100 mL portions of water, dried and evaporated. The residue (6.5 g) was chromatographed using 5–20% ethyl acetate in hexane. This produced 4.78 g of oily product; $^1$H NMR (CDCl$^3$) δ1.78–1.98 (m,12H), 2.67 (br s,1H), 3.34 (br s,1H), 3.55 (t,2H), 3.69 (t,2H), 4.91 (br s,1H), 6.77–7.19 (m,4H).

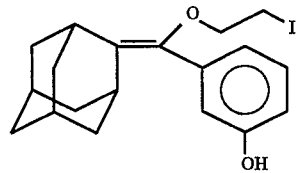

(e) Synthesis of [(3-hydroxyphenyl)-(2-iodoethoxy)methylene]tricyclo[3.3.1.1$^{3,7}$]decane. The chloroethoxy alkene (2 g) was dissolved in 30 mL of anhydrous acetone. Sodium iodide (9.3 g) was added and the solution refluxed for 4 days. After cooling, the precipitate was filtered and washed with a little CH$_2$Cl$_2$. The washings and acetone were combined and evaporated. The residue was redissolved in CH$_2$Cl$_2$ and washed with water and dried. The crude material was chromatographed using 25% ethyl acetate in hexane. The yield was 93% of a slightly yellow oil; $^1$H NMR (CDCl$_3$) δ1.78–1.98 (m, 12H), 2.65 (br s,1H), 3.19 (t,2H), 3.35 (br s,1H), 3.69 (t,2H), 4.90 (br s,1H), 6.75–7.24 (m,4H).

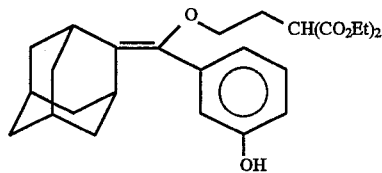

(e) Synthesis of [((3,3-biscarboethoxy)propoxy)-(3-hydroxy-phenyl)methylene]tricyclo[3.3.1.1$^{3,7}$]decane. Diethyl malonate (3.12 g) was dissolved in 25 mL of absolute ethanol containing 11.65 mL of a 21% solution of sodium ethoxide in ethanol. The solution was cooled in an ice bath and the iodoethoxy alkene (3.2 g) was added dropwise as an ethanol solution to the reaction mixture. The reaction was refluxed over night. After cooling, the mixture was evaporated and redissolved in ethyl acetate. The ethyl acetate solution was extracted with water, dried and evaporated. The crude material was chromatographed using 15–25% ethyl acetate in hexane. The yield of product was typically 42–48%; $^1$H NMR (CDCl$_3$) δ1.24 (t,6H), 1.78–1.97 (m, 12H), 2.11–2.17 (q,2H), 2.66 (br s,1H), 3.21 (br s,1H), 3.42 (t,2H), 3.63 (t,1H), 4.13–4.22 (m,4H), 5.00 (br s,1H), 6.75–7.21 (m,4H).

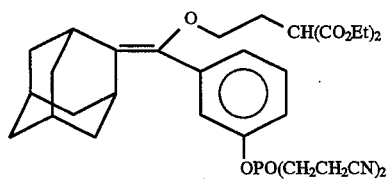

(f) Synthesis of [((3,3-biscarboethoxy)propoxy)-(3-(bis-(2-cyanoethyl)phosphoryloxy)phenyl)methylene]tricyclo

[3.3.1.1³,⁷]decane. A flask containing 30 mL of CH₂Cl₂ under a layer of argon was cooled in an ice bath. Pyridine (6.95 mL) was added followed by slow addition of POCl₃ (2.47 mL) and stirring continued for 15 min. A solution of the alkene from step (e) in 10 mL of CH₂Cl₂ and 5 mL of pyridine was added dropwise. The ice bath was removed and the solution stirred for 2 hours. To this solution was added 6.95 mL of pyridine and 6.1 g of 2-cyanoethanol. The reaction mixture was stirred over night resulting in formation of a yellow precipitate. The mixture was added to 200 mL of CH₂Cl₂ and washed with 3×75 mL of water. The CH₂Cl₂ extract was dried and evaporated. The crude product was purified by chromatography using 70% ethyl acetate in hexane. $^1$H NMR (CDCl₃) δ1.25 (t,6H), 1.74–1.98 (m, 12H), 2.10–2.17 (q,2H), 2.61 (br s,1H), 2.81 (t,4H), 3.21 (br s,1H), 3.42 (t,2H), 3.59 (t,1H), 4.11–4.22 (m,4H), 4.39–4.46 (m,4H), 7.14–7.36 (m,4H).

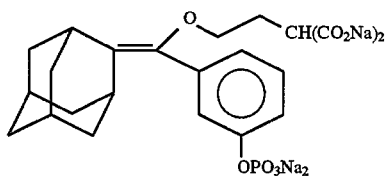

(g) Synthesis of [(3,3-biscarboxypropoxy)-(3-phosphoryloxyphenyl)methylene]tricyclo[3.3.1.1³,⁷]decane, tetrasodium salt. The alkene (3.9 g) from step (f) was dissolved in 12 mL of acetone. A solution of 1.04 g of sodium hydroxide in 3 mL of water was added. The solution was stirred for 19 hours during which time 3 mL of acetone was added to the flask. The liquid was decanted and the solid washed with more acetone. After drying under vacuum, a white solid was obtained. $^1$H NMR (D₂O) δ1.72–2.07 (m, 14H), 2.59 (br s,1H), 3.14–3.18 (m,2H), 3.40 (t,2H), 7.01–7.34 (m,4H).

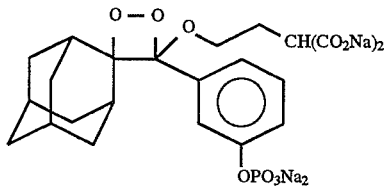

(h) Synthesis of [4-(3,3-biscarboxy)propoxy)-4-(3-phosphoryloxyphenyl)]spiro[1,2-dioxetane-3,2'-tricyclo[3.3.1.1³,⁷]decane], tetrasodium salt. The alkene (2.5 g) from step (g) was dissolved in 50 mL of D₂O. Polymer-bound Rose Bengal (500 mg) was suspended in 50 mL of p-dioxane and added to the water solution. The reaction mixture was cooled to 5°–7° C., oxygen bubbling was started and the mixture irradiated with a sodium lamp through a 5 mil sheet of KAPTON (DuPont). After a total of 18 hours, the polymer beads were filtered off, the vessel was washed with methanol and the combined solution concentrated to 25 mL. The remaining solvent was removed by lyophilization.

Example 2

Preparation of Dioxetane 3

This dioxetane was prepared by the sequence of reactions described below. The synthesis up to the intermediate alkene [(3-carboxypropoxy)-(3-hydroxyphenyl)methylene]-tricyclo-[3.3.1.1³,⁷]decane was conducted essentially as described in published European Patent Application No. 91113601.8.

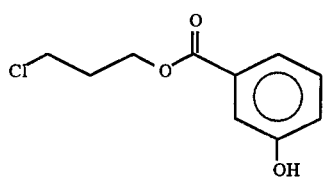

(a) Synthesis of 3-chloropropyl 3-hydroxybenzoate. 3-Chloro-1-propanol (161.6 g, 1.71 mol) was refluxed with 3-hydroxy-benzoic acid (40.0 g, 0.29 mol) and a catalytic amount of sulfuric acid for a total of 9 hours. The excess alcohol was removed by vacuum distillation. The resulting orange oil was diluted with 400 mL of water and neutralized to pH 7. The solution was extracted with ethyl acetate (3×250 mL). The organic layer was washed with 100 mL of brine and dried over anhydrous sodium sulfate, filtered and concentrated under reduced pressure. The product was purified by column chromatography with to give 67.5 g of product which contained a small amount of the starting alcohol: $^1$H NMR (CDCl₃) δ2.24 (quint, 2H), 3.70 (t, 2H), 4.48 (t, 2H, J=6 Hz), 5.55 (s, 1H), 7.05–7.63 (m, 4H).

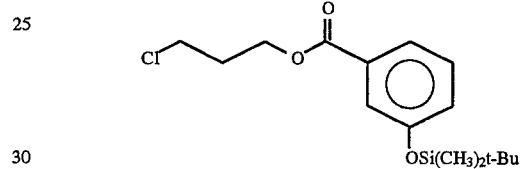

(b) Synthesis of 3-chloropropyl 3-(tert-butyldimethylsiloxy)benzoate. 3-Chloropropyl 3-hydroxybenzoate (67.5 g) was dissolved in anhydrous DMF (100 mL) followed by and t-butyl-dimethylsilyl chloride (52.11 g). The reaction mixture was stirred under Ar until the starting material was consumed. The reaction mixture was diluted with water (500 mL) and extracted with hexane (4×750 mL) and then with 2×250 mL of ethyl acetate. The combined organic solutions were dried over sodium sulfate, concentrated under reduced pressure and partitioned a second time between 500 mL of water and hexane. Drying the organic solution and evaporating gave the silylated ester as white crystals (89.64 g, 94%). $^1$H NMR (CDCl₃) δ0.219 (s, 6H), 0.998 (s, 9H), 2.24 (quint, 2H), 3.70 (t, 2H), 4.470 (t, 2H), 7.03–7.64 (m, 4H).

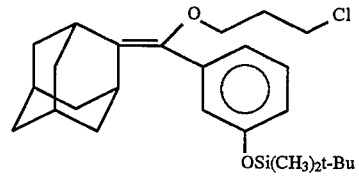

(c) Synthesis of [(3-tert-butyldimethylsilyloxylphenyl)-(3-chloropropoxy)methylene]tricyclo[3.3.1.1³,⁷]decane. Titanium trichloride (25.8 g, 0.167 mol) was added to dry THF (500 mL) in a dried 3 L three-necked flask under a head of Ar at 0° C. Lithium aluminum hydride (3.01 g, 0.084 mol) was added in small portions with vigorous stirring. The reaction mixture was warmed to room temperature and 23.3 mL of triethylamine was added dropwise. After the addition was completed, the reaction mixture was refluxed for 2 h. Heating was stopped and a solution of 3-chloropropyl 3-(tert-butyldimethylsilyloxy)benzoate (5.28 g, 0.016 mol) and adamantanone (7.23 g, 0.048 mol) in 100 mL of dry THF was added dropwise to the refluxing mixture over a 45 min period. The reaction mixture was stirred over night at room temperature. The black mixture was diluted with water and extracted with 3×300 mL of hexane. The combined organic solutions were filtered, dried over sodium sulfate and concentrated under reduced pressure. The residue was partially purified by flash chromatography (2% ethyl acetate/hexane) to give the product as a viscous oil which was taken on to the next step. 1H NMR (CDCl₃) δ0.200 (s, 6H), 0.988 (s, 9H), 1.66–2.01 (m, 14H), 2.63 (br s, 1H), 3.23 (br s, 1H), 3.538 (t, 2H, J=5.7 Hz), 3.640 (t, 2H, J=6.6 Hz), 6.75–7.22 (m, 4H).

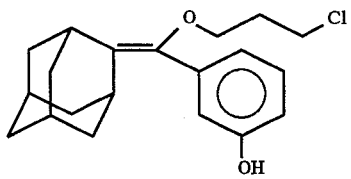

(d) Synthesis of [(3-Chloropropoxy)-(3-hydroxyphenyl)-methylene]tricyclo[3.3.1.1³,⁷]decane. The silyl-protected alkene (5.36 g slightly impure) was dissolved in 75 mL of dry THF and placed under Ar. TBAF (4.16 g, 13.2 mmol) was added and the reaction mixture stirred for 30 min at room temperature. The solvent was evaporated and the residue was dissolved in 100 mL of water. The solution was extracted with 3×125 mL of ether and the organic layer was washed with brine and dried over Na₂SO₄. Removal of solvent under reduced pressure and column chromatography with 10% ethyl acetate in hexane afforded 2.05 g of the deprotected alkene. ¹H NMR (CDCl₃) δ1.78–2.01 (m, 14H), 2.65 (br s, 1H), 3.22 (br s, 1H), 3.541 (t, 2H, J=6 Hz), 3.644 (t, 2H, J=6 Hz), 5.30 (s, 1H), 6.75–7.24 (m, 4 H).

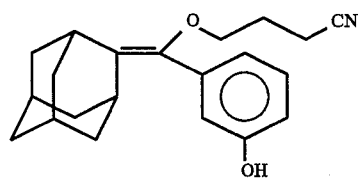

(e) Synthesis of [(3-cyanopropoxy)-(3-hydroxyphenyl)-methylene]tricyclo[3.3.1.1³,⁷]decane. Sodium cyanide (300 mg, 6.1 mmol) was added to a solution of the chloroalkene (815 mg, 2.4 mmol) in anhydrous DMSO (4 mL) forming a purple solution which was heated to 120° C. for 1 hr. The cooled solution was diluted with ether (50 mL) and washed with water (3×25 mL). The ether layer was dried and concentrated under reduced pressure. The product was obtained as an oil in 85% yield. ¹H NMR (CDCl₃) δ1.77–1.97 (m, 14H), 2.49 (t, 2H), 2.65 (br s, 1H), 3.19 (br s, 1H), 3.49 (t, 2H), 5.04 (s, 1H), 6.75–7.24 (m, 4H).

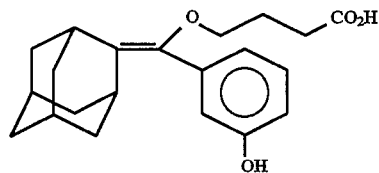

(f) Synthesis of [(3-carboxypropoxy)-(3-hydroxyphenyl)-methylene]tricyclo[3.3.1.1³,⁷]decane. Sodium hydroxide (7 mL of 2N solution) was added to the nitrile (0.67 g, 2 mmol) and the reaction mixture was refluxed for 36 h. The solution was cooled to room temperature and neutralized with acetic acid (1 eq.). The mixture was extracted with ethyl acetate. The organic layer was washed three times with water, then brine and dried over sodium sulfate. The product was concentrated under reduced pressure to an oil affording the acid (0.64 g, 91%). ¹H NMR (CDCl₃) δ1.78–1.97 (m, 14H), 2.47 (t, 2H), 2.65 (br s, 1H), 3.22 (br s, 1H), 3.45 (t, 2H), 5.83 (s, 1H), 6.74–7.22 (m, 4H).

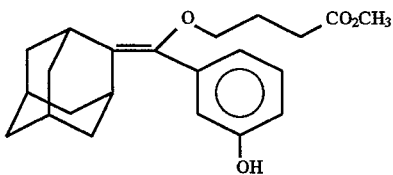

(g) Synthesis of [(3-carbomethoxypropoxy)-(3-hydroxyphenyl)methylene]tricyclo[3.3.1.1³,⁷]decane. The carboxylic acid (660 mg, 1.9 mmol) from the previous step was dissolved in 10 mL of CH₂Cl₂. DCC (597 mg, 2.8 mmol), DMAP (23 mg) and methanol (1 mL) were added and the solution stirred for 18 hours. The mixture was filtered to remove solid material and evaporated. The solid residue was suspended in ether and filtered. The product was purified by column chromatography with 30% ethyl acetate in hexane. ¹H NMR (CDCl₃) δ1.77–1.96 (m, 14H), 2.42 (t, 2H), 2.65 (br s, 1H), 3.22 (br s, 1H), 3.41 (t, 2H), 3.65 (s,3H), 5.15 (br s,1H), 6.74–7.22 (m, 4H).

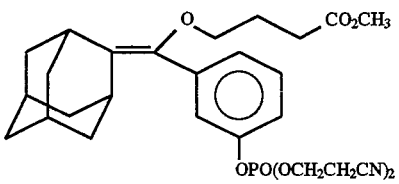

(h) Synthesis of [(3-carbomethoxypropoxy)-(3-(bis-(2-cyanoethyl)phosphoryloxy)phenyl)methylene]tricyclo-[3.3.1.1³,⁷]decane. A flask containing 5 mL of CH₂Cl₂ under a layer of argon was cooled in an ice bath. Pyridine (0.5 mL) was added followed by slow addition of POCl₃ (465 mg) and stirring continued for 15 min. A solution of the alkene (360 mg) from step (g) in 0.5 mL of 1:1 CH₂Cl₂/pyridine was added dropwise. The ice bath was removed and the solution stirred for 135 min. To this solution was added 1.0 mL of pyridine and 0.69 mL of 2-cyanoethanol. The reaction mixture was stirred for 4 hours resulting in formation of a white precipitate. TLC showed formation of two materials. Adding an additional 200 µL of cyanoethanol caused the precipitate to dissolve but stirring over night was without effect. The solution was evaporated to dryness and the crude product purified chromatographically. ¹H NMR (CDCl₃) δ1.79–1.98 (m, 14H), 2.41 (t,2H), 2.61 (br s,1H), 2.80 (m,4H), 3.23 (br s,1H), 3.41 (t,2H), 3.65 (s,3H), 4.32–4.48 (m,4H), 7.15–7.37 (m,4H).

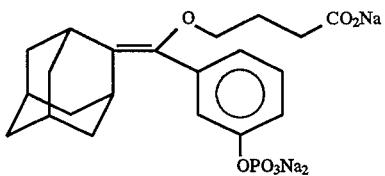

(i) Synthesis of [(3-carboxypropoxy)-(3-phosphoryloxyphenyl)methylene]tricyclo[3.3.1.1³,⁷]decane, trisodium salt. The alkene (142 mg) from step (h) was dissolved in 4 mL of acetone. A solution of 36.4 mg of sodium hydroxide in <1 mL of water was added. The solution was stirred for 20 hours causing formation of a precipitate. The liquid was decanted and the solid washed with more acetone followed by methanol. After drying under vacuum, 100 mg of a white solid was obtained. $^1$H NMR (D$_2$O) δ1.71–1.95 (m,14H), 2.23 (t,2H), 2.62 (br s,1H), 3.18 (br s,1H), 3.53 (t,2H), 7.04–7.36 (m,4H).

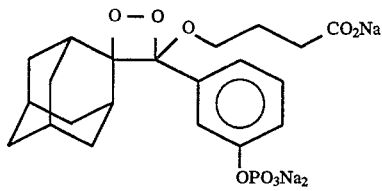

(j) Synthesis of [4-(3-carboxypropoxy)-4-(3-phosphoryloxyphenyl)]spiro[1,2-dioxetane-3,2'-tricyclo[3.3.1.1$^{3,7}$]-decane]. The alkene (26.8 mg) from step (i) was dissolved in 1.5 mL of D$_2$O. Polymer-bound Rose Bengal (75 mg) was suspended in 1.5 mL of p-dioxane-d$_8$ and added to the water solution. The reaction mixture was cooled to 5°–7° C., oxygen bubbling was started and the mixture irradiated with a sodium lamp through a 0.005" sheet of KAPTON. After a total of 30 min, $^1$H NMR indicated the reaction to be complete (disappearance of peak at δ2.6) so the polymer beads were filtered off.

Example 3

Discovery of Reagent Carryover Problem in Capsule Chemistry Analysis System

The experiments described below were performed on a prototype capsule chemistry analysis system essentially as described by Kumar et al in U.S. Pat. No. 5,399,497, with the detection system configured to measure light emission (luminescence). The method and apparatus comprises feeding a stream of fluid segments through a Teflon tube, where the tube has an isolating layer of fluorocarbon oil on the inner surface. Sample and reagents are aspirated into this tube, and the resulting liquid segments are moved through the tube. Separation steps and washing steps which are required by heterogeneous immunoassay methods were facilitated by means of magnets, which transferred magnetic particles from one aqueous segment to another. The detection system was comprised of a photon counter and a fiber optic read head, in which the fibers were radially arranged around the Teflon tube to maximize the efficiency of light collection.

The TECHNICON IMMUNO 1® TSH method (Bayer Corporation, Tarrytown, N.Y., USA) was used as a representative immunoassay method for the testing of luminogenic reagents. The method principle involved incubation of a specimen containing the antigen TSH with a first reagent (R1), which contained a fluorescein-labeled antibody, and simultaneously with a second reagent (R2), which contained an antibody-alkaline phosphatase (ALP) conjugate. Each antibody was specific for a different epitope on the TSH antigen, so that formation of a "sandwich" was promoted between these two antibodies and the TSH antigen. Magnetic particles containing bound anti-fluorescein were used to capture the sandwich, and the particles were subsequently washed to remove unbound reagents. The particles were then exposed to the luminogenic reagent, which contained a substrate for ALP, and luminescence was measured.

The luminogenic R3 reagent was comprised of 0.2 mM CSPD (disodium 3-(4-methoxyspiro{1,2-dioxetane-3,2'-(5'-chloro)tricyclo [3.3.1.1$^{3,7}$]decan}-4-yl)phenyl phosphate, (Tropix, Inc., Bedford, Mass., USA), 3 mM pyranine (hydroxypyrenesulfonic acid), 1 mM MgCl$_2$, 1M diethanolamine buffer (pH 10.0), 0.1% Triton X-100 and 0.1% NaN$_3$. The sequence of events on the capsule chemistry analysis system is depicted in FIG. 1 of the drawings. The fluid capsule or test package was comprised of six liquid segments, each of which had a volume of 28 μl. Magnetic particles (1.4 μl of the magnetic particle reagent used in the TECHNICON IMMUNO 1 system were aspirated into the first segment (MP), with the remainder of fluid being particle wash buffer (25 mM Tris, pH 7.5, containing 0.2M NaCl, 0.1% Triton X-100 and preservative). R1 (10.4 μl of serum-based solution containing fluorescein-labeled antibody to TSH), R2 (10.4 μl of serum-based solution containing antibody to TSH conjugated with ALP) and S (7.2 μl of serum sample) were aspirated into the second segment. The next two segments (W1 and W2) were comprised of the same wash buffer used above in the MP segment. The fifth segment was R3, of the composition described above, with the key elements being the luminogenic substrate and the luminescence enhancer. The sixth segment was an inter-test buffer (same as the particle buffer described above), which was used to isolate adjacent tests. Magnetic transfers are depicted by the arrows in the FIG. 1. These transfers were facilitated by one of two magnetic transfer assemblies (M1 or M2). After an incubation of 13 minutes, during which sandwich formation occurred, M1 transferred the magnetic particles into the R1+R2+S segment to initiate capture. After an additional period of 6 minutes, M2 transferred the particles into the first wash segment. After an additional period of 12 seconds, M2 transferred the particles into the second wash segment. After another period of 12 seconds, M2 transferred the particles into the R3 segment, and light emission from this segment was detected as the stream of aqueous segments passed back and forth through the luminometer readhead.

Figure 2:
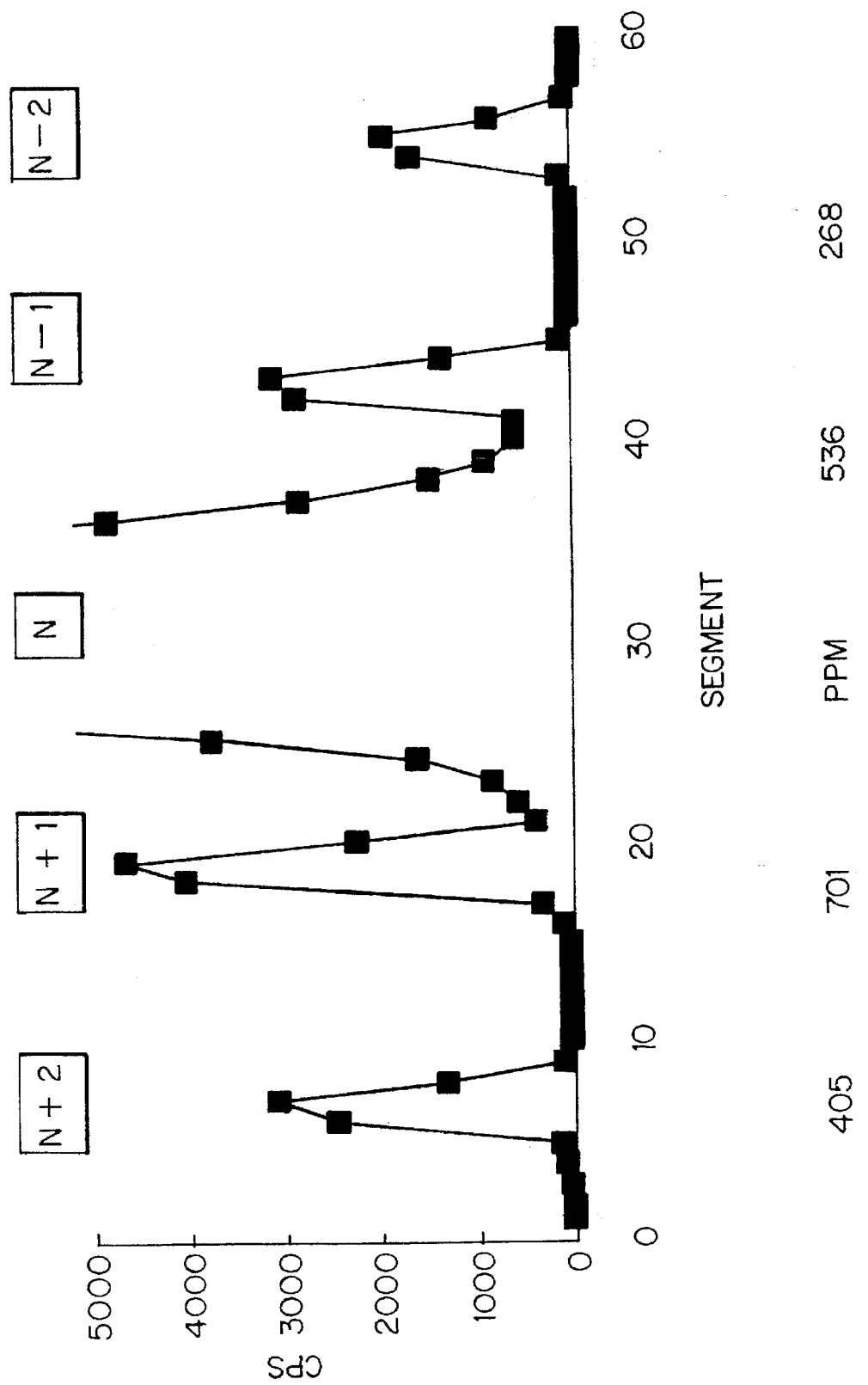
FIG. 2 is a profile of adjacent segments in the capsule chemistry analysis system showing the observed luminescence attributed to carryover as more fully described in the Examples below.

Since the Teflon tube is transparent to light, a problem with light piping (or "optical carryover") was expected. Specifically, some of the photons emitted from the R3 segment of an adjacent test could enter the Teflon material, propagate down the length of the tube and be scattered into the detector during the measurement of the signal of the test of interest. However, while a signal was detected in the adjacent tests, it did not occur in the expected manner. Instead of declining rapidly with distance from test N, peaks of light output were observed centered around the R3 segments of the adjacent test packages, as shown in FIG. 2 of the drawings. In FIG. 2, test N produced a high level of luminescence, approximately 7.5 million counts per seconds (cps). Tests N−1 and N−2 were aspirated into the tube before test N and preceded this test through the luminometer, and tests N+1 and N+2 followed after test N. The analysis system recorded photons counted for each individual air and liquid segment in the stream. The profile in FIG. 2 represents the average of 10 replicate panels of 5 tests each corrected for background luminescence signal produced in the absence of ALP. The reagent blank values subtracted from each data point were an average obtained from 10 replicate panels of 5 tests each. The magnitude of the carryover signal was computed by dividing the peak cps in each adjacent test by the peak cps in test N, expressed in parts per million (ppm).

Another possible explanation for this behavior was physical carryover of ALP from test N into the neighboring tests in an unintended manner. This could happen, for example, if the tube contained particulate materials deposited on the walls, which could disrupt the smooth motion of the liquid segments through the tube. However, placement of 10 mM inorganic phosphate in the R3 segments of the adjacent tests had no effect on the magnitude of the signals in the adjacent tests. Since this amount of phosphate would have inhibited ALP by at least 90% under these test conditions, the possibility of physical carryover was ruled out.

Figure 3:
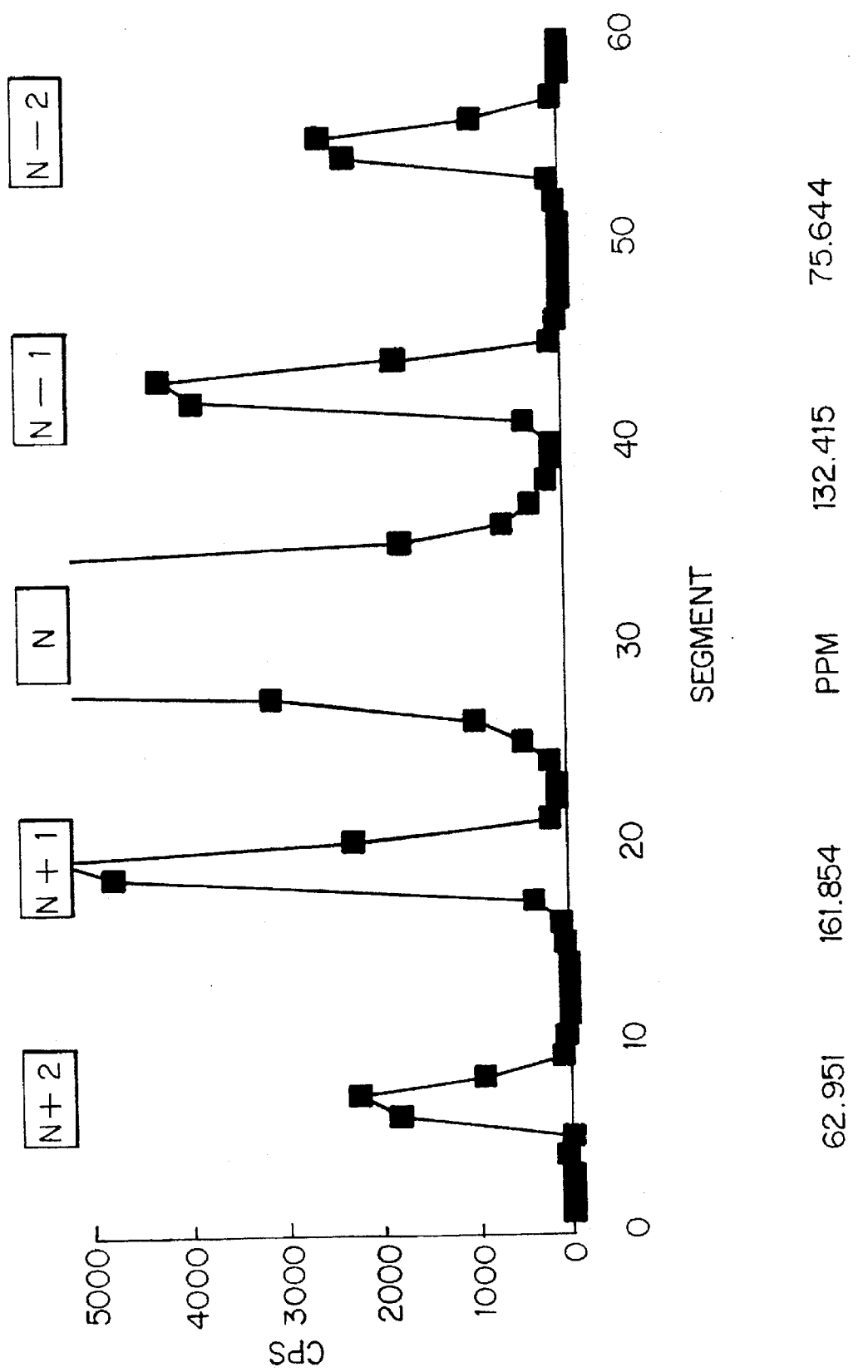
FIG. 3 is a further profile of adjacent segments observed in the experiments which are more fully described in the Examples below and which established that the carryover was not optical in nature.

To further rule out optical carryover, the fluorescent enhancer pyranine was omitted from test N only, but present in the adjacent tests. As a result, the magnitude of the signal in test N was lower by a factor of approximately 10. However, as shown in FIG. 3 of the drawings, the height of the peaks in the adjacent tests did not change significantly. The fact that the carryover signal did not change in the adjacent tests proportionately clearly demonstrated that this carryover was not optical.

An additional and unexpected type of carryover was the cause of the carryover problem. It was found that the hydroxy dioxetane intermediate was sufficiently soluble in the fluorocarbon oil used to coat the inner wall of the Teflon tube, such that the carryover was due to transfer of dissolved hydroxy dioxetane intermediate via the oil into the R3 segments of the neighboring tests. This process was tested by changing the buffer of the R3 segments in the adjacent tests from 1M DEA at pH 10 to 1M Tris at pH 7. At pH 7, dissolved hydroxy dioxetane intermediate in these R3 segments is stable and does not emit light. As shown in FIG. 4 of the drawings, this change in pH resulted in the complete elimination of the side bands of luminescence. The residual minor carryover in the N+1 and N−1 tests was due to the anticipated optical carryover. These results verified that the source of light emission in the peaks in the neighboring tests was "chemical carryover" of the hydroxy dioxetane derived from CSPD into the R 3 segments of adjacent tests.

Example 4

Elimination Of Observed Chemical Carryover with Dicarboxylic Acid-substituted Dioxetane 1

Table 1 shows the effect of using three other dioxetanes on the chemical carryover of the reaction intermediate. LUMIGEN PPD [4-(methoxy)-4-(3-phosphoryl-oxyphenyl)]-spiro [1,2-dioxetane-3,2'-tricyclo[3.3.1.1$^{3,7}$]-decane], (Lumigen, Inc., Southfield, Mich., USA), dioxetane 3, a monocarboxylic acid derivative and dioxetane 1, a dicarboxylic acid derivative were each used in test formulations at the same concentration. The ppm column is the signal for the N+1 test, which represents worst case behavior. The carryover of the unmodified parent compound, PPD, was found to be more than twice as high as that observed with CSPD. Surprisingly, the monocarboxylic acid derivative, dioxetane 3, showed a reduction of only 84% in the magnitude of the chemical carryover. This indicated that a single charged group was insufficient to completely prevent solubilization of the reaction intermediate in the fluorocarbon oil. However, the dicarboxylic acid derivative was 100% effective, indicating that two charged groups were fully adequate to achieve the desired behavior.

TABLE 1

Reduction of Chemical Carryover

| Compound | ppm | % Reduction |
|---|---|---|
| LUMIGEN PPD | 1640 | |
| Dioxetane 3 | 260 | 84 |
| Dioxetane 1 | 0 | 100 |

Example 5

The Role of Enhancers

As part of the optimization of a reagent based on dioxetane 1, a number of enhancer materials was examined. At pH 9.6, enhancer A (1-trioctylphosphoniummethyl-4-tributylphosphoniummethylbenzene dichloride) increased the luminescent signal by a factor of 6.2, and enhancer B (poly(vinylbenzyltributylphosphonium chloride)) increased the signal by a factor of 19.7. At pH 10.0, enhancer A increased the signal by a factor of 4.8, and enhancer B increased the signal by a factor of 18.9.

Despite the fact that enhancer B achieved higher light intensities, enhancer A was preferred for use on the analysis system since it is a low molecular weight monomeric compound. Polymeric compounds, especially if they are polycationic, interact with serum components, causing precipitation, which would pose significant problems for the operation of the analysis system.

Both fluorescein and pyranine were found to be effective as supplementary fluorescers in combination with enhancer A. Alone, these fluorescers must be used at relatively high concentrations (3 mM) in order to achieve an enhancement of about ten-fold. However, in combination with enhancer A, a synergistic effect was observed, in which a comparable enhancement resulted at 100-fold lower concentrations of fluorescer than needed in the absence of the enhancer. Tables 2 and 3 show the extent of enhancement by pyranine and fluorescein, respectively, in the presence of 1 mg/ml of enhancer A.

TABLE 2

Enhancement by Pyranine with Enhancer A

| [Pyranine] (mM) | Enhancement Factor |
|---|---|
| 0.01 | 3.7 |
| 0.02 | 7.3 |
| 0.03 | 9.8 |
| 0.04 | 12.2 |
| 0.05 | 13.7 |

TABLE 3

Enhancement by Fluorescein with Enhancer A

| [Fluorescein] (mM) | Enhancement Factor |
|---|---|
| 0.01 | 2.6 |
| 0.02 | 4.0 |
| 0.05 | 7.1 |
| 0.10 | 8.7 |

Example 6

Optimized Formulation for Capsule Chemistry Analysis System

The above described observations have led to the development of an optimized formulation for the capsule chemistry analysis system. This formulation is comprised of 0.1–1 mM dioxetane 1, 0–0.05 mM pyranine, 0.1–5 mg/mL Enhancer A, 0–1 mM Mg$^{+2}$, 0.1–1M 2-amino-2-methyl-1-propanol (pH 10.0) and 0.01–1% Triton X-100. Use of this formulation results in complete elimination of the chemical carryover problem and enhanced performance.

The foregoing examples are illustrative only and not to be restrictive. The scope of the invention is indicated only by the appended claims.

What is claimed is:

1. In a capsule chemistry analytical assay method wherein fluid capsules are flowed through a conduit, such fluid capsules comprising discrete isolated aqueous segments separated by an oil-based isolating fluid, and wherein at least one of said discrete segments contains a chemiluminescent dioxetane reagent, and at least one other of such discrete segments contains an activating agent which reacts with the dioxetane reagent to produce light, the improvement which comprises employing, as the chemiluminescent dioxetane reagent, a stable dioxetane of the formula:

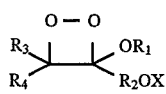

wherein $R_1$ is a hydrophilic organic group comprising a substituted alkyl, heteroalkyl, alkenyl or alkynyl group containing 1 to 20 carbon atoms and at least two ionic groups which provide increased solubility in aqueous solution and optionally containing at least one oxygen atom, wherein $R_3$ and $R_4$ are each selected from the group consisting of acyclic, cyclic and polycyclic organic groups which can optionally be substituted with heteroatoms and which can optionally be joined together to form a cyclic or polycyclic ring group spiro-fused to the dioxetane ring, wherein $R_2$ is an aryl ring group selected from the group consisting of phenyl and naphthyl groups which can include additional substituents and wherein X is a protecting group which can be removed by an activating agent to produce light.

2. The method of claim 1 for performing a capsule chemistry heterogeneous immunoassay wherein at least one of said discrete segments contains an immunoreagent labeled with an enzyme as said activating agent.

3. The method of claim 2 wherein the dioxetane reagent has the formula:

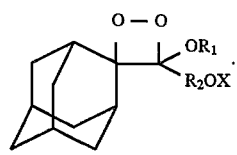

4. The method of claim 1 wherein said fluid capsules are reversibly flowed through said conduit.

5. The method of claim 1 wherein $R_3$ and $R_4$ together form a cyclic or polycyclic alkyl group which is spiro-fused to the dioxetane ring and which contains 6 to 30 carbon atoms and which can optionally include additional substituents.

6. The method of any one of claims 1, 2, 4, 5 or 3 wherein the ionic groups which provide increased solubility are selected from the group consisting of carboxylate, sulfonate, sulfate, phosphate, phosphonate, nitrate, trialkylammonium, trialkylphosphonium, dialkylsulfonium and guanidinium groups.

7. The method of claim 6 wherein the ionic groups which provide increased solubility are carboxylate groups.

8. The method of claim 7 wherein the OX group is selected from the group consisting of an $O^-M^+$ group wherein M is selected from the group consisting of hydrogen, an alkali metal ion, a quaternary ammonium and a quaternary phosphonium ion, an $OOCR_8$ group wherein $R_8$ is selected from the group consisting of alkyl and aryl groups containing 2 to 8 carbon atoms and optionally containing heteroatoms, $OPO_3^{-2}$ salt, $OSO_3^{31}$ salt, β-D-galactosidoxy and β-D-glucuronidyloxy groups.

9. The method of claim 1 wherein the dioxetane has the formula:

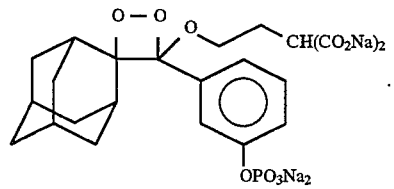

10. The method of claim 1 wherein at least one of said discrete segments contains an enhancer substance which increases the quantity of light produced upon reaction of the dioxetane reagent with the activating agent.

11. The method of claim 10 wherein the enhancer substance is non-polymeric and cationic.

12. The method of claim 10 wherein the enhancer substance is a dicationic surfactant of the formula:

$$Y^-\ R\ _3A^{30}CH_2\text{-Link-}CH_2A^{30}R_3Y^-$$

wherein each of A is independently selected from the group consisting of P and N atoms, wherein Link is an organic linking group containing at least two carbon atoms selected from the group consisting of substituted and unsubstituted aryl, alkyl, alkenyl and alkynyl groups, wherein Link can optionally contain heteroatoms, wherein R is selected from the group consisting of lower alkyl and aralkyl groups containing 1 to 20 carbon atoms and wherein Y is an anion.

13. The method of claim 10 wherein the enhancer substance is a dicationic surfactant of the formula:

$$Cl^{31}\ (n\text{-}C_4H_9)_3P^{30}CH_2\text{-Link-}CH_2P^{30}(n\text{-}C_8H_{17})_3\ Cl^{31}$$

and wherein link is phenylene.

14. The method of any one of claims 10, 11, 12 or 13 wherein the dioxetane has the formula:

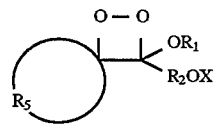

wherein $R_5$ is selected from the group consisting of cyclic and polycyclic alkyl groups which are spiro-fused to the dioxetane ring and which contain 6 to 30 carbon atoms and which can optionally include additional substituents.

15. The method of claim 14 wherein $R_5$ is selected from the group consisting of an adamantyl group and a substituted adamantyl group.

16. The method of claim 14 wherein the dioxetane has the formula:

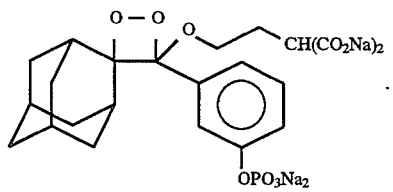

17. The method of claim 10 wherein the dioxetane has the formula:

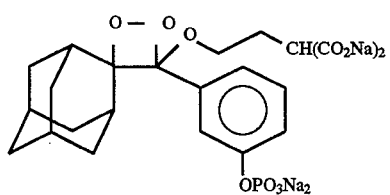
and the enhancer substance is 1-trioctylphosphoniummethyl-4-tributylphosphoniummethylbenzene dichloride.
* * * * *

UNITED STATES PATENT AND TRADEMARK OFFICE
CERTIFICATE OF CORRECTION

PATENT NO. : 5,631,167
DATED : May 20, 1997
INVENTOR(S) : Robert F. Adolphsen, Hashem Akhavan-Tafti, Renuka DeSilva, and A. Paul Schapp It is certified that error appears in the above-indentified patent and that said Letters Patent is hereby corrected as shown below:

In column 8, line 18, delete "$Y^-R_3A^{30}CH_2\text{-Link-}CH_2A^{30}R_3Y^-$", and insert -- $Y^-R_3\overset{+}{A}CH_2\text{-Link-}CH_2\overset{+}{A}R_3Y^-$ -- therefor.

In column 8, line 29, delete "$Cl^-(n\text{-}C_4H_9)_3P^{30}CH_2\text{-Link-}CH_2P^{30}(n\text{-}C_8H_{17})_3Cl^-$", and insert -- $Cl^-(n\text{-}C_4H_9)_3\overset{+}{P}CH_2\text{-Link-}CH_2\overset{+}{P}(n\text{-}C_8H_{17})_3Cl^-$ -- therefor.

In column 20, line 1, delete "$OSO_3^{31}$", and insert -- $OSO_3^-$ -- therefor.

In column 20, line 23, delete "$Y^-R_3A^{30}CH_2\text{-Link-}CH_2A^{30}R_3Y^-$", and insert -- $Y^-R_3\overset{+}{A}CH_2\text{-Link-}CH_2\overset{+}{A}R_3Y^-$ -- therefor.

In column 20, line 36, delete "$Cl^{31}(n\text{-}C_4H_9)_3P^{30}CH_2\text{-Link-}CH_2P^{30}(n\text{-}C_8H_{17})_3Cl^{31}$", and insert -- $Cl^-(n\text{-}C_4H_9)_3\overset{+}{P}CH_2\text{-Link-}CH_2\overset{+}{P}(n\text{-}C_8H_{17})_3Cl^-$ -- therefor.

UNITED STATES PATENT AND TRADEMARK OFFICE
CERTIFICATE OF CORRECTION

PATENT NO. : 5,631,167
DATED : May 20, 1997
INVENTOR(S) : Robert F. Adolphsen, Hashem Akhavan-Tafti, Renuka DeSilva, and A. Paul Schapp It is certified that error appears in the above-indentified patent and that said Letters Patent is hereby corrected as shown below:

In column 2, line 57, delete "there use", and insert -- their use -- therefor.

In column 15, line 67, delete "decan", and insert -- decane -- therefor.

Signed and Sealed this

Eighteenth Day of August, 1998

Attest:

BRUCE LEHMAN

Attesting Officer     Commissioner of Patents and Trademarks